United States Patent [19]

Ando et al.

[11] Patent Number: 5,198,419

[45] Date of Patent: Mar. 30, 1993

[54] FORMULATED MEDICINES FOR ENHANCING THE EFFICACY OF BETA-LACTAM ANTIBIOTICS IN PROPHYLAXIS AND TREATMENT AGAINST INFECTIOUS DISEASE DUE TO PATHOGENIC BACTERIA

[75] Inventors: Kunio Ando, Kawasaki; Sachiko Goto, Chiba, both of Japan

[73] Assignee: Immuno Japan Inc., Tokyo, Japan

[21] Appl. No.: 769,766

[22] Filed: Oct. 4, 1991

Related U.S. Application Data

[63] Continuation-in-part of Ser. No. 624,229, Dec. 7, 1990, abandoned.

[30] Foreign Application Priority Data

Dec. 8, 1989 [JP]  Japan .................................. 1-319463

[51] Int. Cl.$^5$ ...................... A61K 37/02; A61K 31/43; A61K 31/545; C07K 13/00
[52] U.S. Cl. .......................................... 514/8; 514/12; 514/192; 514/200; 530/832; 424/439; 426/532; 426/657
[58] Field of Search .................. 514/2, 8, 12, 192, 200; 530/350, 395, 832; 424/439; 426/532, 657

[56] References Cited

U.S. PATENT DOCUMENTS

| | | | |
|---|---|---|---|
| 4,153,686 | 5/1979 | Nagel | 424/176 |
| 4,668,771 | 5/1987 | Kawakami et al. | 514/21 |
| 4,726,948 | 2/1988 | Prieels et al. | 426/648 |
| 4,977,136 | 12/1990 | Nichols et al. | 514/6 |
| 5,019,411 | 5/1991 | Johnson et al. | 426/52 |

OTHER PUBLICATIONS

*The Merck Manual*, Berkow, Editor, pp. 98, 2305–2311, 1982.

Arnold et al., *Infection and Immunity* 28:893–898, Jun. 1980.

Mochizuki et al., *Antimicrobial Agents and Chemotherapy* 32: 1648–1654, Nov. 1988.

Primary Examiner—Robert A. Wax
Assistant Examiner—Stephen Walsh
Attorney, Agent, or Firm—Beveridge, DeGrandi, Weilacher & Young

[57] ABSTRACT

Lactoferrin can be used to increase the efficacy of beta-lactam antibiotics. There is a potentiating effect when lactoferrin is administered either simultaneous with or shortly before or after the administration of beta-lactam antibiotics. The dosage of lactoferrin administered is usually 0.5–100 mg/kg and preferably 1–10 mg/kg.

20 Claims, 2 Drawing Sheets

FORMULATED MEDICINES FOR ENHANCING THE EFFICACY OF BETA-LACTAM ANTIBIOTICS IN PROPHYLAXIS AND TREATMENT AGAINST INFECTIOUS DISEASE DUE TO PATHOGENIC BACTERIA

REFERENCE TO RELATED APPLICATIONS

This application is a continuation-in-part of U.S. patent application Ser. No. 07/624,229, which is relied on and incorporated by reference.

INTRODUCTION AND BACKGROUND

The present invention relates to formulated medicines for potentiation of the clinical efficacy of beta-lactam antibiotics, both to prevent and treat infectious disease caused by pathogenic bacteria. The formulated medicines of the present invention contain bovine milk lactoferrin and show remarkable potentiating effect on the clinical efficacy of beta-lactam antibiotics, thus more effectively preventing and treating bacterial diseases of mammals, including human beings. The present invention also relates to a method for the prevention and treatment of bacterial diseases in mammals, including human beings.

Lactoferrin is the major glycoprotein present in the granules of mature neutrophils and is deemed to be one of the host-defense factors, being locally released where pathogenic bacteria infect. Lactoferrin also exists in such diverse secretions as milk, tears, saliva, and digestive juices, and is thought to be one of the factors which prevent mammals from being infected by bacterial pathogens. The function of lactoferrin is not clear but is believed to play a similar role to that of lysozyme and secretory immunoglobulin A. The most important role of lactoferrin is considered to be the covering and protecting of mucous membranes which occupy huge areas on the body surface which are always being threatened by the invasive attack of bacterial pathogens.

Therefore, lactoferrin is regarded as a nonspecific barrier against the invasion of pathogenic bacteria. It probably cooperates with other host-defense factors such as phagocytes, lysozyme, complement and immunoglobulins. In a healthy human adult male, five grams of lactoferrin are produced daily (calculated on the basis of the turnover rate of neutrophils). As it is well known, when acute inflammation caused by bacterial infection occurs, the productivity of lactoferrin increases by approximately six fold to 30 g per day. For this reason lactoferrin is deemed to play a very important role in host-defense mechanisms against bacterial infection and its importance is comparable to such host-defense factors as phagocytes, immunoglobulins and lysozyme.

In mammals, milk, especially colostrum, contains a large amount of lactoferrin. The reason why colostrum contains such large amounts is that it probably protects newborn infants from many kinds of infectious pathogens because a fetus grows aseptically in the maternal uterus and never encounters such kinds of bacterial pathogens before birth. They are highly susceptible to infection by such agents because of the immature properties of their host-defense system. Their gastrointestinal system is free from bacteria at birth and the normal intestinal flora is not formed soon after birth. The role of milk lactoferrin is likely, in cooperation with other host-defense factors, to cover intestinal mucosa, thus protecting the intestine from invasion by pathogenic bacteria and to help the newborns to form normal intestinal microflora.

However, it is not clear how and where lactoferrin acts on the surface of mucosa. Although a number of studies have been conducted during the past two decades, the functions and roles of lactoferrin have not yet been clarified. Moreover, it is unknown what kinds of physiological or pharmacological responses occur on the animal level when lactoferrin derived from other animal species is given orally to another animal species. Bovine milk lactoferrin used in this invention is a minor component of whey protein and it has been very expensive when isolated in relatively pure form. Whey, especially cheese whey, is the most abundant natural source of lactoferrin. Cheese whey is a typical byproduct in dairy industry and major portions of it have been wasted for swine feed or direct spray on meadows as fertilizer.

However, owing to the development of new technology, e.g., large scale separation and purification techniques using ultrafiltration membranes and ion exchange column chromatography, such minor but bioactive proteins as lactoferrin can be efficiently extracted and isolated in native form from whey (which contains numerous minor ingredients). Therefore, relatively pure lactoferrin (approximately more than 85% pure) is now available at a reasonable cost. Nevertheless, these advances are worthless without development of a potential usefulness for lactoferrin. Two reasons are considered why the biomedical utilization of lactoferrin has been hindered. The first reason is a possibility of anaphylactic shock since the bovine lactoferrin is non-self for human beings, so that parenteral administration may result in induction of severe anaphylactic shock when repeatedly administered. Therefore, at the present time, the route of administration of bovine lactoferrin has to be strictly limited to oral administration for human beings. The second reason stems from the possibility of the digestibility of lactoferrin by proteinase in the gastrointestinal tract. When bovine lactoferrin was orally taken by mammals, it is useless when it is hydrolyzed in the gastrointestinal tract to constituent amino acids and peptides before reaching the active site.

Recent immunology studies indicate that macromolecules with non-self antigenic determinants are occasionally absorbed through the intestine where suppressor T-cells recognize them as non-self and suppress helper T-cell proliferation, thus leading to inhibition of the immunological responses to the non-self antigens. That is to say, when intact non-self antigen is absorbed though the intestine without changing the structure, a kind of immunological tolerance is induced.

Therefore, as far as the oral route is concerned, bovine lactoferrin never induces anaphylactic shock in humans even if small portions are absorbed through the intestine without changing its complete structure. Thus, the oral route is the safest way to dose antigenic macromolecules. Moreover, bovine lactoferrin molecules are highly resistant to gastrointestinal digestion and, when taken orally, considerable amounts are excreted in intact form in feces.

According to previous studies, lactoferrin is an antibacterial protein present in the granules of neutrophils and its activity is dependent on the degree of iron saturation; the activity of iron-free lactoferrin, apolactoferrin, is the most potent and its activity is gradually lost as the degree of the saturation elevates. However, the present invention has revealed (as shown in table 1) that even apolactoferrin from bovine milk lacks antibacterial activity in vitro against most pathogenic bacteria. Most of the bacteria showed minimum inhibitory concentrations of more than 6,400 μg/ml, the only exception is *Streptococcus epidermidis* ATCC 13288 whose growth was inhibited in the presence of 800 μg/ml of apolactoferrin; such concentrations are unattainably high at the whole animal level. Therefore, even though the lactoferrins have very weak antibacterial activity in vitro, it is questionable that they exert direct antibacterial activity against bacteria infecting mammals.

SUMMARY OF THE INVENTION

One object of the present invention was to develop efficient drug formulations in order to prevent and treat infectious diseases caused by pathogenic bacteria in mammals, including human beings. Another object was to develop a new method for the prevention and treatment of bacterial diseases and to potentiate the efficacy of beta-lactam antibiotics.

DETAILED DESCRIPTION OF THE INVENTION

Figure 1:
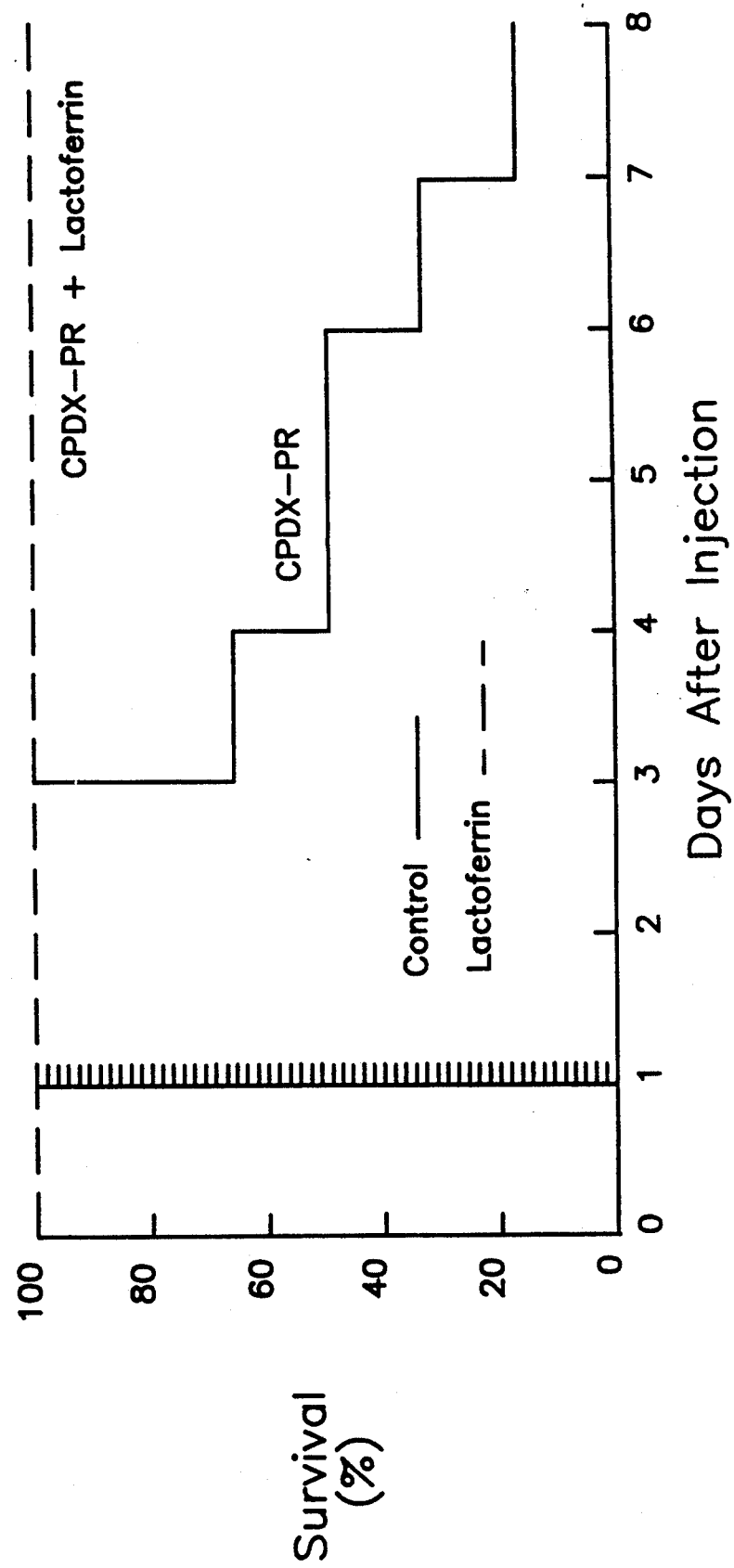
FIG. 1 illustrates the results of Example 1; p.o. means oral administration. The data for the control and lactoferrin groups indicate that all mice in those groups died by one day post-injection of the bacteria.

In this invention the present inventors have found that bovine milk lactoferrin potentiates the efficacy of beta-lactam antibiotics at the whole animal level during studies on experimental infections in mice. As shown in Table 3, simultaneous oral administration of beta-lactam antibiotics with lactoferrin to mice one hour after intraperitoneal injection of *Klebsiella pneumoniae* strain 3K25 resulted in potentiation of the antibiotic efficacy 2.8 fold greater than the antibiotic treatment alone.

The characteristics of this potentiating effect by bovine lactoferrin on the efficacy of beta-lactam antibiotics are as follows: (1) the combination shows this effect with both penicillin and cephalosporin families of beta lactam antibiotics, and (2) the potentiating effect is observed not only in mice but also in human and other animal species.

Thus lactoferrin and beta lactam antibiotics can be utilized in the prevention and treatment of bacterial disease caused by beta-lactam sensitive bacteria.

Co-administration of lactoferrin with beta-lactam antibiotics greatly reduces the antibiotic requirement, that is, ½ to 1/6 of the amount of the antibiotics required in monotherapy in combination with lactoferrin (combined therapy) show the same curative effects as the antibiotic treatment alone (monotherapy). Oral administration of lactoferrin is an effective route, and the dose of lactoferrin required for this potentiation is 0.5-100 mg/kg and the optimum dose may be 1-10 mg/kg.

Lactoferrin isolated from either milk or neutrophils is able to chelate two ferric ions per molecule to form an iron complex. Native lactoferrin isolated from cheese whey is iron-unsaturated; the degree of saturation is only 25-30%. Lactoferrin releases chelated ferric ions in acidic conditions below pH 3.0 and becomes iron-free apolactoferrin.

Apolactoferrin can be utilized as a raw material to prepare lactoferrin with desired degrees of iron-saturation by adding calculated amounts of ferric ions in the presence of carbonium anions. The present inventors have confirmed, through a study using 100%, 28% and 0% iron-saturated lactoferrin, that the degree of iron-saturation does not affect the potentiation of the efficacy of beta-lactam antibiotics. Therefore, lactoferrins with various degrees of iron-saturation can be successfully utilized in this invention. The efficacy potentiation of beta-lactam antibiotics by lactoferrin is independent of the degree of the iron-saturation of lactoferrin.

The stability of bovine lactoferrin powder is also not affected by the degree of iron-saturation. It is very stable at room temperature and is readily formulated into tablets, granules, tincture, syrup, and powder. Much care should be taken to avoid lactoferrin denaturation, especially denaturation by heat, in any formulating process. Due to its high stability, it is readily processed into mixed formulations with beta-lactam antibiotics for oral administration in any proportion, for example, freely mixed with lactose, cellulose, cellulose derivatives, magnesium stearate, and talc. One of the best ways to make lactoferrin liquid formulations, such as tincture and syrup, is adjustment of the pH to pH 3.1-4.0 by the addition of lactic acid to avoid bacterial contamination, then add paraaminobenzoic acid derivatives as preservatives against fungal contamination, and filtration through membrane filters (e.g., with pore size of 0.2 μm) into aseptic bottles.

When lactoferrin is orally dosed to potentiate the efficacy of beta-lactam antibiotics, either the combined formulation with the antibiotics or the formulation containing lactoferrin alone as an active ingredient can be successfully used. When lactoferrin is dosed separately from the antibiotics, the timing of the dosing is very important. The potentiating effect is the strongest when lactoferrin is given from six hours before to one hour after the antibiotic administration. A significant but less potent effect is observed when lactoferrin is given at 12 hours before or six hours after the antibiotic administration.

When administering lactoferrin to mammals orally, any formulated form may be used; e.g., tablets, granules, powder, syrup and so on.

Lactoferrin can be utilized when mixed with foods, e.g., supplemented with milk, yoghurt, skim milk powder, lactic acid bacteria fermented milk, chocolates, tablet sweets, and powdered beverages. The presence of lactoperoxidase in the food is not required. The most important factor for producing lactoferrin-containing foods is to avoid protein denaturation during processing by not exceeding a temperature of about 60° C. The pharmaceutical composition of this invention may contain the active compounds together with a solid or liquid pharmaceutically acceptable non-toxic carrier. Such pharmaceutical carriers can be sterile liquids, such as water and oils, including those of petroleum, animal, vegetable or synthetic origin, such as peanut oil, soybean oil, mineral oil, sesame oil and the like. Saline solution and aqueous dextrose and glycerol solutions can also be employed as liquid carriers. Suitable pharmaceutical excipients include starch, glucose, lactose, sucrose, gelatin, malt, rice flour, chalk, silica gel, magnesium carbonate, magnesium stearate, talc, sodium chloride, dried skim mild, glycerol, propylene glycol, water, ethanol, and the like.

These compositions can take the form of solutions, suspensions, tablets, pills, capsules, powders, sustained release formulations and the like. Suitable pharmaceutical carriers are described in "Remington's Pharmaceutical Science" by E. W. Martin. Such compositions will contain an effective therapeutic amount of the active compound together with a suitable amount of carrier so as to provide the form for proper administration to the host. The only route for administering lactoferrin is oral one, and other modes can not be employed.

EXAMPLES

For $ED_{50}$ values, a range of amounts of antibiotics is given in the examples (e.g., penicillin G: 0.4, 0.2, 0.1, 0.05 mg/mouse). To calculate the $ED_{50}$, groups of mice in the monotherapy groups and groups of mice in the combined therapy groups received the indicated amount of antibiotic (e.g., one group received 0.4 mg/mouse of penicillin G, one group received 0.2 mg/mouse of penicillin G, one group received 0.1 mg/mouse of penicillin G, one group received 0.05 mg/mouse of penicillin G).

EXAMPLE 1

Sixty male mice, strain ICR, four weeks of age, body weight $19\pm1.0$ g (mean±the standard deviation) were randomly divided into ten groups (n=6); the first group was assigned to the untreated control, the second group to the lactoferrin treated control group, the third through the sixth groups to the cephalosporin treated controls, and the seventh through the tenth groups to the combined treatment group of cephalosporin and lactoferrin. The mice were intraperitoneally injected with pneumobacillus, *Klebsiella pneumoniae* strain 3K25, $5\times10^6$ colony forming units (CFU) per mouse. The antibiotics used were orally active cephalosporin or cefpodoxime, and the bovine lactoferrin was the native one derived from cheese whey with 28.5% iron-saturation. One hour after the injection, the untreated control was orally given 0.2 ml of physiological saline, the second group orally given lactoferrin (0.4 mg/mouse), the third through the sixth groups were orally given cefpodoxime (10, 5, 2.5 and 1.25 mg/mouse) in 0.2 ml of physiological saline, the seventh through the tenth groups orally given the admixture of cefpodoxime (5, 2.5, 1.25, and 0.625 mg/mouse) together with lactoferrin (0.4 mg/mouse) in 0.2 ml of the saline. All the mice were housed in an animal room, allowed free access to commercial pellet diet and water, and observed for one week.

All the mice in the untreated control group and the lactoferrin treated control group died within 24 hours after the injection due to septicemia, while in the cefpodoxime treated group and the combined treatment groups the life span was significantly prolonged in comparison with the untreated control group and the lactoferrin treated control group. The $ED_{50}s$ (calculated according to Van der Wearden's method) of the two cefpodoxime treated groups described above were 7.93 mg/mouse (6.3-10.0 mg/mouse) for cefpodoxime alone and 1.25 mg/mouse (0.92-1.70 mg/mouse) for the combined therapy of cefpodoxime with lactoferrin. As shown in FIG. 1, the results suggest that the simultaneous administration of lactoferrin with cephalosporin antibiotics remarkably potentiates the antibiotic efficacy, thus reducing the antibiotic requirement.

Figure 2:
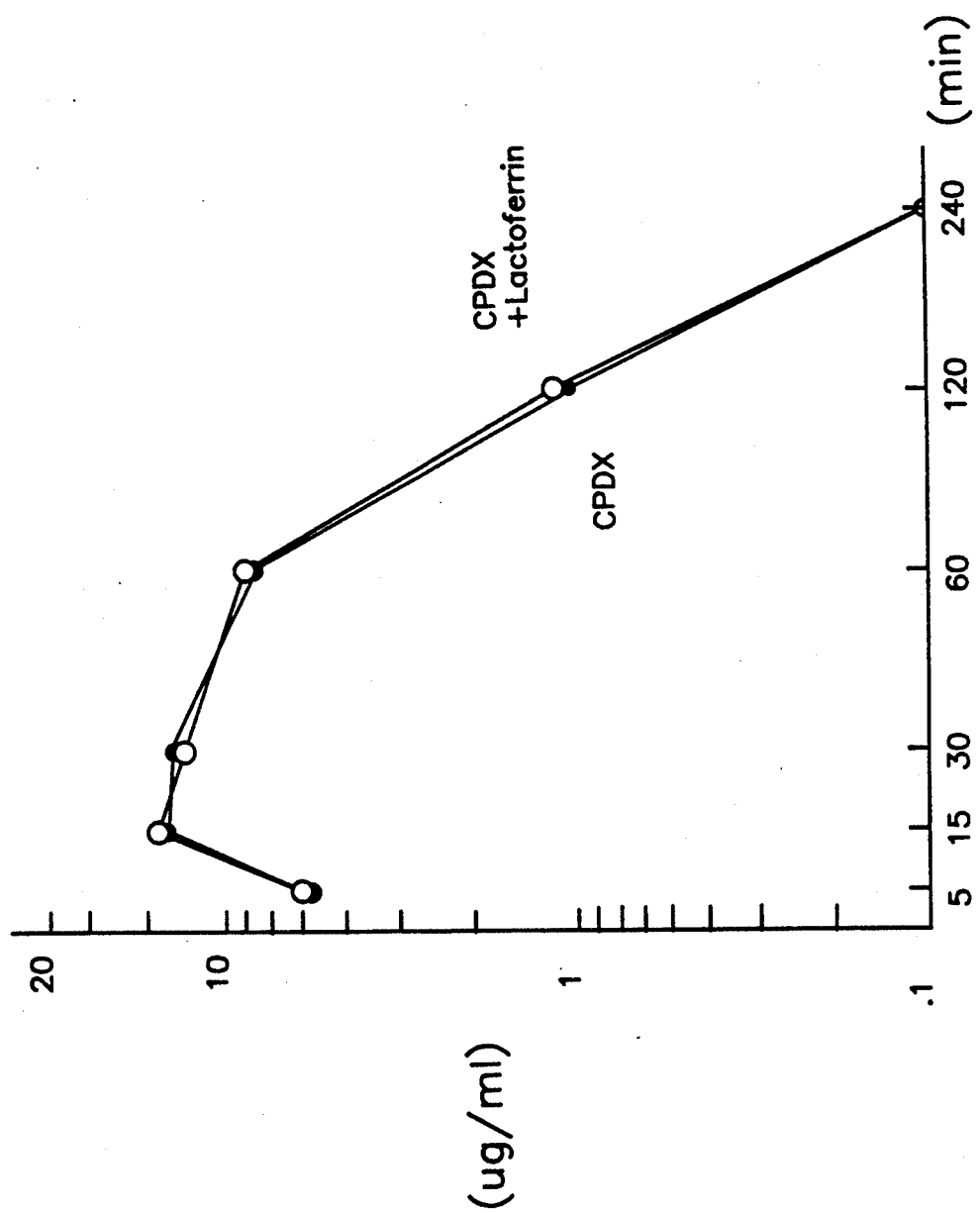
FIG. 2 shows the concentration of cefpodoxime in the blood of two groups of mice (cefpodoxime group; cefpodoxime and lactoferrin group) taken at 5, 15, 30, 60 and 120 minutes after oral administration. One group received 0.5 mg/mouse of cefpodoxime; the other group received 0.5 mg/mouse of cefpodoxime and 0.5 mg/mouse of lactoferrin.

One possible explanation of this extraordinary and unexpected phenomena is that co-administration of lactoferrin with cefpodoxime greatly enhances the antibiotic absorption through the gut, thereby elevating its blood concentration. However, this possibility was excluded by comparing the concentrations in the bloods of both groups (i.e., cefpodoxime alone; cefpodoxime and lactoferrin) taken at 5, 15, 30, 60 and 120 minutes after the administration (see FIG. 2). The most plausible mechanism is that lactoferrin activates the nonspecific host defense system against bacterial infection, thus more efficiently killing bacteria, in cooperation with much smaller amount of beta-lactam antibiotics.

EXAMPLE 2

Sixty male mice, strain ICR, five weeks of age, weighing $19.3\pm1.1$ g (mean body weight±the standard deviation) were randomly allocated into ten groups (n=6), and intraperitoneally injected with pneumobacilli, *Klebsiella pneumoniae* strain 3K25, $5\times10^5$ CFU/mouse. One hour after the injection, the first group was orally given 0.2 ml of physiological saline, the second group orally given iron free apolactoferrin (0.4 mg) in 0.2 ml of saline, the third through the sixth groups were orally given cefpodoxime (4, 2, 1, and 0.5 mg/mouse) in 0.2 ml saline, and the seventh through the tenth groups orally given the admixture of cefpodoxime (4, 2, 1, and 0.5 mg/mouse) and apolactoferrin (0.4 mg) in 0.2 ml of saline. Mice were fed ad libitum and observed for a week under the same conditions as described in Example 1.

All the mice died within 24 hours in the untreated control group and the lactoferrin treated control group, and again all the mice reco ered from the invention in the combined therapy group. The $ED_{50}s$ of the two cefpodoxime treated groups were 0.99 mg/mouse (0.74-1.32 mg/mouse) for the monotherapy group and 0.25 mg/mouse (0.19-0.33 mg) for the combined therapy group.

EXAMPLE 3

Sixty male mice, strain ICR, five weeks of age, weighing $21.3\pm1.5$ g (mean±the standard deviation) were randomly allocated into ten groups (n=6), and intraperitoneally injected with *Klebsiella pneumoniae* strain 3K25, $1\times10^6$ CFU/mouse. One hour after the injection, the first group was orally given 0.2 ml of physiological saline, the second group orally given hololactoferrin (100% ferric ion saturated lactoferrin, 0.4 mg/mouse), the third through the sixth groups orally given cefaclor (2.0, 1.0, 0.5 and 0.25 mg/mouse each) in 0.2 ml of saline, and the seventh through the tenth groups orally given cefaclor (2.0, 1.0, 0.5 and 0.25 mg/mouse each) and hololactoferrin (100% iron saturated lactoferrin, 0.4 mg/mouse) in 0.2 ml of saline. The mice were fed ad libitum and observed for one week under the same conditions as described in Example 1. All the mice in the untreated control group and the hololactoferrin treated control group died within 24 hours and the $ED_{50}s$ of the two cefaclor groups were 0.63 mg/mouse for the monotherapy group and 0.30 mg/mouse for the combined therapy group.

EXAMPLE 4

The experimental design is similar to that of Example 3. The mice groups (n=6) were intraperitoneally injected with *Klebsiella pneumoniae* strain 3K25, $1 \times 10^6$ CFU/mouse, and one hour after the injection, orally active cephalosporin, cefotetan (2.0, 1.0, 0.5 and 0.25 mg/mouse) was orally administered with or without native lactoferrin (0.4 mg/mouse) in 0.2 ml physiological saline. All the mice died within 24 hours in the untreated control group. The $ED_{50}$s of two cefotetan groups were 0.50 mg/mouse for the monotherapy group and 0.16 mg/mouse for the combined therapy group.

EXAMPLE 5

Gastric emptying greatly affects intestinal absorption of some kinds of drugs, especially lipophilic ones in which the absorption is much accelerated by the presence of foods in the stomach. Orally active cephalosporins are relatively lipophilic, so that it was anticipated that the absorption rate is much slower under fasting condition.

Male mice, strain ICR, five weeks old, weighing an average of 21.6 g, were randomly allocated into sixteen groups (n =6). During the next 24 hours, eight groups were allowed free access to diet and water, while the other eight groups were fasted overnight. On the next day, all the mice were injected with $1.4 \times 10^6$ CFU/mouse of *Klebsiella pneumoniae* strain 3K25. The minimal lethal dose of this bacterium is $1.0 \times 10^3$ CFU/mouse, and thus the injected dose was 1,000 times greater than the minimal lethal dose. Immediately after the injection, the fed groups were orally given cefpodoxime (10, 5, 2.5, and 1.25 mg/mouse) simultaneously with or without native lactoferrin (0.2 mg/mouse). The fasted groups also were orally given cefpodoxime (10, 5, 2.5, and 1.25 mg/mouse) simultaneously with or without native lactoferrin (0.2 mg/mouse). The $ED_{50}$ s of these groups are shown in Table 2.

The $ED_{50}$s of the fed groups were much smaller than those of the corresponding fasted groups, suggesting that the bioavailability of cefpodoxime is greater in the fed condition than in the fasted one. Also the results indicate that lactoferrin significantly potentiates the antibiotic efficacy either under fed or fasted conditions, though the rate of potentiation is much greater in the fasted state (five fold) than in the fed state (three fold).

EXAMPLE 6

Male mice, strain ddY, five weeks old, weighing an average of 21.5 g, were randomly allocated into groups (n=10), and they were intraperitoneally injected with *Escherichia coli* #11, $1.2 \times 10^6$ CFU/mouse. Immediately after the injection, the untreated control group was orally given 0.2 ml of distilled water, the second through the fifth groups were treated once orally by ampicillin (8, 4, 2 and 1 mg/mouse), and the sixth through the ninth groups with ampicillin (4, 2, 1 and 0.5 mg/mouse) plus apolactoferrin (1 mg/mouse) in 0.2 ml of distilled water. The mice were fed ad libitum and observed for one week under the same conditions as described in Example 1. The $ED_{50}$s were 6.02 mg/mouse for the monotherapy group, and 0.75 mg/mouse for the combined therapy group, indicating that the simultaneous administration of lactoferrin with ampicillin also significantly potentiates ampicillin efficacy in vivo by eight fold. It is apparent from the results that lactoferrin not only potentiates the efficacy of the cephalosporin class but also the penicillin class of antibiotics.

EXAMPLE 7

Male mice, strain ddY, five weeks old, were randomly allocated into groups (n=10), and were intraperitoneally injected with *Proteus mirabilis* GN79 ($1.3 \times 10^6$ CFU/mouse) or with *Escherichia coli* #11 ($1.7 \times 10^6$ CFU/mouse) or with *Klebsiella pneumoniae* 3K25 ($1.5 \times 10^6$ CFU/mouse). The doses are 1,000 times greater than the minimum lethal dose. Immediately after the injection, the first eight groups were orally given ampicillin, the second eight groups were orally given cephalexin, and the third eight groups were orally given cefaclor, respectively, each simultaneously with or without native lactoferrin (1 mg/mouse) in 0.2 ml of distilled water (see Table 7). All the mice were fed ad libitum and observed for one week under the same conditions as described in Example 1.

As shown in Table 3, when lactoferrin was orally given to the mice immediately after the bacterial injections, the combined treatment significantly potentiates the antibiotic efficacy by 2.8 to 6.2 fold as compared with the treatment with the antibiotics alone.

EXAMPLE 8

The dose-response relationship of the potentiation of the antibiotic efficacy by lactoferrin was determined using the same experimental infection system as described in Example 1. Male ddY mice, five weeks of age, weighing approximate 20.3 g, were randomly allocated into groups (n=10); the first group was assigned to the cefpodoxime control (5 mg/mouse). The mice were intraperitoneally injected with pneumobacillus, *Klebsiella pneumoniae* strain 3K25, $3 \times 10^5$ per mouse. One hour after the injection, the antibiotic cefpodoxime (1, 0.5, 0.25 and 0.125 mg/mouse) was orally given in 0.2 ml of physiological saline. As shown in Table 4, lactoferrin doses from 50 to 0.05 mg per mouse significantly potentiated the antibiotic efficacy at the same magnitude regardless of the dose, indicating the potentiation reaches a plateau with a dose of 0.05 mg per mouse.

EXAMPLE 9

The effect of time-schedule of lactoferrin administration on the potentiation of antibiotic efficacy was examined using an experimental model similar to Example 1. Male ddY mice (n=10), five weeks old, weighing an average of 21.9 g, were used in this experiment. Lactoferrin (0.5 mg/mouse) was orally administered once according to the time-schedule shown in Table 5. On day 0 all the mice were intraperitoneally injected with $1.2 \times 10^5$ CFU/mouse of *Staphylococcus aureus* 209P. Amoxicillin (5, 2.5, 0.25, 0.625 mg/mouse) was orally given one hour after the injection.

As shown in Table 5, lactoferrin significantly potentiated the amoxicillin's efficacy when dosed from 12 hours before to three hours after the injection. Therefore this potentiation of antibiotic efficacy by oral lactoferrin is not always dependent on simultaneous dosing with beta-lactam antibiotics.

EXAMPLE 10

The potentiation of antibiotic efficacy by lactoferrin was examined using an infection model similar to Example 1. The antibiotics and lactoferrin were administered immediately after the injection (see Table 8). Table 6 shows the results. Lactoferrin (0.4 mg/mouse) potentiates the efficacies of the four beta-lactam antibiotics used: penicillin G against *Streptococcus pyogenes* infection was potentiated by 4.6 fold, cefazolin against *S. epidermidis* by 3.1 fold, methicillin against *Diplococcus pneumoniae* by 3.7 fold, and cloxacillin against *Pseudomonas aeruginosa* by 3.0 fold. Therefore, lactoferrin potentiates the efficacy of beta-lactam antibiotics against diseases caused by both gram-positive and gram-negative pathogenic bacteria.

EXAMPLE 11

Seventeen patients (male 6, female 11, an average 63.5 years old) with chronic urinary tract infection were randomly allocated into two groups. All these patients excreted at least one species of bacteria in their urine for longer than four weeks, although they were treated orally with antibacterial agents. The first group (n=9) was treated for four weeks with 1,200 mg of cefaclor (400 mg, three times a day) and the second group (n=8) with the same dose of cefaclor (three times a day) combined with 600 mg of apolactoferrin (200 mg, three times a day). Urine specimens were collected every one week and the species of bacteria were identified and the quantity of excreted bacteria determined. Four weeks later, bacteria were no longer detected in the urine of the combined treatment group, while six patients out of nine in the monotherapy group still excreted bacteria, indicating that the combined therapy is significantly more effective than the monotherapy.

Further variations and modifications of the invention will become apparent to those skilled in the art from the foregoing and are intended to be encompassed by the claims appended hereto.

The Japanese Priority Application filed on Dec. 8, 1989 is relied on and incorporated by reference.

TABLE 1

The minimum inhibitory concentration of apolactoferrin against bacteria on the agar-plate medium.

| Name of Pathogenic Bacterium | Minimum Inhibitory Conc. (µg/ml) | Name of Pathogenic Bacterium | Minimum Inhibitory Conc. (µg/ml) |
| --- | --- | --- | --- |
| *Staphylococcus aureus* 209p | >6,400 | *Proteus mirabilis* GN79 | >6,400 |
| *Staphylococcus aureus* Smith | >6,400 | *Proteus mirabilis* 1287 | 3,200 |
| *Staphylococcus aureus* 227 | >6,400 | *Proteus vulgaris* IFO 3851 | >6,400 |
| *St. epidermidis* ATCC 13288 | 800 | *Proteus vulgaris* GN76 | >6,400 |
| *Micrococcus lutens* ATCC 9341 | >6,400 | *Pr. morganii* IFO 3848 | >6,400 |
| *Bacillus subtilis* ATCC 6633 | 3,200 | *Pr. morganii* GN125 | 3,200 |
| *Enterobacter feacalis* 64 | 3,200 | *Pr. rettgeri* IFO 13501 | 3,200 |
| *Enterobacter feacalis* 95-1 | 3,200 | *Pr. rettgeri* GN624 | 6,400 |
| *Escherichia coli* NIHJ JC-2 | 3,200 | *Pr. inconstans* IFO 12930 | >6,400 |
| *Escherichia coli* C11 | >6,400 | *Pr. inconstans* GN 627 | >6,400 |
| *Escherichia coli* No 35 | 1,600 | *Citrobacter freundii* GN 346 | >6,400 |
| *Klebsiella pneumoniae* GN69 | >6,400 | *Citrobacter freundii* 2 | >6,400 |
| *Kleb. pneumoniae* ATCC 10031 | >6,400 | *Enterobacter cloacae* No 91 | >6,400 |
| *Kleb. pneumoniae* 3K25 | >6,400 | *Serratia marcescens* No 2 | >6,400 |
| *Kleb. pneumoniae* IFO 3512 | >6,400 | *Ser. marcescens* IFO 12648 | >6,400 |
| *Klebsiella oxytoca* 1006 | >6,400 | *Serratia marcescens* No 78 | >6,400 |
| *Shigella sonnei* | >6,400 | *Pseudomonas aeruginosa* E 7 | >6,400 |
| *Shigella flexineri* | >6,400 | *Pseu. aeruginosa* TMS 11 | >6,400 |
| *Salmonella typhi* | >6,400 | *Pseu. aeruginosa* IFO 3445 | >6,400 |
| *Salmonella paratyphi* A | >6,400 | *Pseu. aeruginosa* No. 11 | >6,400 |
| *Salmonella paratyphi* B | >6,400 | *Pseu. aeruginosa* No. 47 | >6,400 |
| *Vibrio cholerae* 569B | 3,200 | | |

TABLE 2

Effect of lactoferrin on $ED_{50}$ of cefpodoxime in experimentally infected fed and fasted mice.

| groups | $ED_{50}$ (mg/mouse) | |
| --- | --- | --- |
| | fasted | fed |
| admixture of lactoferrin | 7.80 (5.65–10.83) | 4.90 (3.65–6.60) |
| antibiotic alone | 39.40 (27.15–56.15) | 15.65 (11.45–21.30) |

TABLE 3

Effect of lactoferrin on $ED_{50}$ of oral penicillin and cephalosporins in experimentally infected mice.

| Antibiotics | Administration | Pathogen | Amount of In infection (CFU/mouse) | $ED_{50}$ (mg/kg) |
| --- | --- | --- | --- | --- |
| Ampicillin | alone | *Proteus mirabilis* GN79 | $1.3 \times 10^6$ | 133.0 |
| | with lactoferrin | *Proteus mirabilis* GN79 | $1.3 \times 10^6$ | 24.9 |
| Cephalexin | alone | *Escherichia coli* #11 | $1.7 \times 10^6$ | 215.6 |
| | with lactoferrin | *Escherichia coli* #11 | $1.7 \times 10^6$ | 34.8 |
| Cefaclor | alone | *Klebsiella pneumoniae* 3K25 | $1.5 \times 10^6$ | 28.5 |
| | with lactoferrin | *Klebsiella pneumoniae* 3K25 | $1.5 \times 10^6$ | 10.0 |

TABLE 4

The dose-response relationship of potentiation of antibiotic efficacy by oral lactoferrin treatment

| lactoferrin (mg/mouse) | $ED_{50}$ (mg/mouse) |
| --- | --- |
| 50.0 | 0.104 |
| 5.0 | 0.104 |
| 0.5 | 0.104 |
| 0.05 | 0.104 |
| 0.005 | 0.382 |
| 0.00 | 0.473 |

TABLE 5

The effect of time-schedule of lactoferrin administration on the efficacy of amoxicillin

| lactoferrin dosing on day/hour before or after infection | $ED_{50}$ (mg/mouse) |
|---|---|
| −5 (day) | 2.14 |
| −3 (day) | 2.46 |
| −2 (day) | 2.46 |
| −1 (day) | 1.39 |
| −12 (hr) | 0.55 |
| −6 (hr) | 0.40 |
| 0 | 0.40 |
| +3 (hr) | 0.78 |
| +12 (hr) | 2.48 |
| amoxicillin control | 2.46 |

−5 day: Lactoferrin was orally administered once 5 days before the bacterial infection.
+3: Lactoferrin was orally administered once 3 hours after the bacterial infection.

TABLE 6

Potentiation of antibiotic efficacy by lactoferrin.

| pathogenic bacteria | infected dose | antibiotics | $ED_{50}$ (mg/mouse) control | $ED_{50}$ (mg/mouse) lactoferrin |
|---|---|---|---|---|
| Streptococcus pyogenes #59 | 1000 MLD* | penicillin G (i.p.**) | 0.106 | 0.023 |
| Str. epidermids FT | 1000 MLD | cefazolin (i.p.) | 0.152 | 0.048 |
| Diplococcus pneumoniae Ch | 100 MLD | methicillin (i.p.) | 0.227 | 0.061 |
| Pseudomonas aeruginosa E8 | 10 MLD | cloxacillin (i.p.) | 3.16 | 1.06 |

*minimal lethal dose.
**intraperitoneal injection.

TABLE 7

Antibiotic dose-range in the example 7.

| ampicillin (mg/mouse) | | cephalexin (mg/mouse) | | cefaclor (mg/mouse) | |
|---|---|---|---|---|---|
| single | with LF* | single | with LF* | single | with LF* |
| 10 | 5 | 10 | 5 | 2 | 1 |
| 5 | 2.5 | 5 | 2.5 | 1 | 0.5 |
| 2.5 | 1.25 | 2.5 | 1.25 | 0.5 | 0.25 |
| 1.25 | 0.625 | 1.25 | 0.625 | 0.25 | 0.125 |

LF*; native lactoferrin (1 mg/mouse)

TABLE 8

Antibiotic dose-range in the example 10.

| peniclin G (mg/mouse) | | cefazolin (mg/mouse) | | methicillin (mg/mouse) | | cloxacillin (mg/mouse) | |
|---|---|---|---|---|---|---|---|
| single | +LF* | single | +LF* | single | +LF* | single | +LF* |
| 0.4 | 0.2 | 0.4 | 0.2 | 0.4 | 0.2 | 4.0 | 4.0 |
| 0.2 | 0.1 | 0.2 | 0.1 | 0.2 | 0.1 | 2.0 | 2.0 |
| 0.1 | 0.05 | 0.1 | 0.05 | 0.1 | 0.05 | 1.0 | 1.0 |
| 0.05 | 0.025 | 0.05 | 0.025 | 0.05 | 0.025 | 0.5 | 0.5 |

LF*; native lactoferrin (0.4 mg/mouse)

What is claimed:

1. A pharmaceutical composition enhancing the efficacy of beta-lactam antibiotics in a mammal in need thereof, comprising lactoferrin, at least one beta-lactam antibiotic, and a pharmaceutically acceptable carrier.

2. The pharmaceutical composition according to claim 1, wherein said beta-lactam antibiotic is selected from the group consisting of penicillin class and cephalosporin class beta-lactam antibiotics.

3. The pharmaceutical composition according to claim 1, wherein the weight ratio of lactoferrin:beta-lactam antibiotics is 1:1 to 1:10.

4. The pharmaceutical composition according to claim 1, wherein said lactoferrin is present at a dosage of 0.5–100 mg/kg.

5. The pharmaceutical composition according to claim 4, wherein said lactoferrin is present at a dosage of 1–10 mg/kg.

6. A method for the prevention and treatment of bacterial disease, comprising administering to a mammal in need thereof an amount of the pharmaceutical composition according to claim 1, said amount effective to prevent or treat bacterial disease caused by beta-lactam sensitive bacteria.

7. The method according to claim 6, wherein said administration is oral.

8. The method according to claim 6, where said lactoferrin is present at a dosage of 0.5–100 mg/kg.

9. The method according to claim 8, where said lactoferrin is present at a dosage of 1–10 mg/kg.

10. A method for prevention and treatment of bacterial disease, comprising administering to a mammal in need thereof an amount of lactoferrin and an amount of at least one beta-lactam antibiotic, said amounts effective to prevent or treat bacterial disease caused by beta-lactam sensitive bacteria, wherein said lactoferrin is administered up to 25 hours before or up to two hours after administration of said beta-lactam antibiotic.

11. A method of potentiating the efficacy of a beta-lactam antibiotic to a mammal in need thereof, comprising adding an amount of lactoferrin, effective to potentiate the efficacy of a beta-lactam antibiotic against beta-lactam sensitive bacteria, to at least one beta-lactam antibiotic and a pharmaceutically acceptable carrier, and administering said lactoferrin, beta-lactam antibiotic and carrier to said mammal.

12. A food product which comprises food and an amount of a pharmaceutical composition effective to prevent or treat bacterial disease caused by beta-lactam sensitive bacteria, said pharmaceutical composition comprising lactoferrin, at least one beta-lactam antibiotic, and optionally a pharmaceutically acceptable carrier.

13. The food product according to claim 12, consisting essentially of food and an amount of a pharmaceutical composition effective to prevent or treat bacterial disease caused by beta-lactam sensitive bacteria, said pharmaceutical composition consisting essentially of lactoferrin, at least one beta-lactam antibiotic, and optionally a pharmaceutically acceptable carrier.

14. A method for prevention and treatment of bacterial diseases, comprising administering to a mammal in need thereof an amount of the food according to claim 12, said amount effective to prevent or treat bacterial disease caused by beta-lactam sensitive bacteria.

15. The pharmaceutical composition according to claim 1, wherein said beta-lactam antibiotic is selected from the group consisting of cefotetan, cefpodoxime, ampicillin, cephalexin, cefaclor, penicillin G, cefazolin, methicillin, amoxicillin, and cloxacillin.

16. The pharmaceutical composition according to claim 1, wherein said lactoferrin is hololactoferrin or 25-30% iron saturated lactoferrin.

17. The method according to claim 10, wherein said beta-lactam antibiotic is selected from the group consisting of cefotetan, cefpodoxime, ampicillin, cephalexin, cefaclor, penicillin G, cefazolin, methicillin, amoxicillin, and cloxacillin.

18. The method according to claim 10, wherein said lactoferrin is hololactoferrin or 25-30% iron saturated lactoferrin.

19. The method according to claim 11, wherein said beta-lactam antibiotic is selected from the group consisting of cefotetan, cefpodoxime, ampicillin, cephalexin, cefaclor, penicillin G, cefazolin, methicillin, amoxicillin, and cloxacillin.

20. The method according to claim 11, wherein said lactoferrin is halolactoferrin or 25-30% iron saturated lactoferrin.

* * * * *